United States Patent
Gong

(10) Patent No.: US 10,131,898 B2
(45) Date of Patent: Nov. 20, 2018

(54) BUFFERS FOR USE WITH POLYMERASES

(71) Applicant: Bio-Rad Laboratories, Inc., Hercules, CA (US)

(72) Inventor: Xiao-Song Gong, Richmond, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 362 days.

(21) Appl. No.: 14/805,348

(22) Filed: Jul. 21, 2015

(65) Prior Publication Data

US 2016/0032269 A1 Feb. 4, 2016

Related U.S. Application Data

(60) Provisional application No. 62/027,668, filed on Jul. 22, 2014.

(51) Int. Cl.

| *C12Q 1/68* | (2018.01) |
|---|---|
| *C12P 19/34* | (2006.01) |
| *C12N 9/96* | (2006.01) |
| *C12N 9/12* | (2006.01) |
| *C12Q 1/6844* | (2018.01) |

(52) U.S. Cl.
CPC ............ *C12N 9/96* (2013.01); *C12N 9/1252* (2013.01); *C12P 19/34* (2013.01); *C12Q 1/6844* (2013.01); *C12Y 207/07* (2013.01); *C12Y 207/07007* (2013.01)

(58) Field of Classification Search
None
See application file for complete search history.

(56) References Cited

U.S. PATENT DOCUMENTS

| 4,992,531 | A | * | 2/1991 | Patroni | ................... | C07K 1/113 |
|---|---|---|---|---|---|---|
| | | | | | | 435/69.1 |
| 6,127,155 | A | | 10/2000 | Gelfand et al. | | |
| 6,242,235 | B1 | | 6/2001 | Shultz et al. | | |
| 7,846,703 | B2 | | 12/2010 | Kobayashi et al. | | |
| 7,972,828 | B2 | | 7/2011 | Ward et al. | | |
| 8,404,464 | B2 | | 3/2013 | Ward et al. | | |
| 8,435,741 | B2 | | 5/2013 | Miyoshi et al. | | |
| 2006/0199203 | A1 | * | 9/2006 | Hurt | .................... | C12N 15/1003 |
| | | | | | | 435/6.18 |
| 2008/0064071 | A1 | * | 3/2008 | Hogrefe | ................. | C12Q 1/686 |
| | | | | | | 435/91.2 |
| 2008/0145910 | A1 | | 6/2008 | Ward et al. | | |
| 2009/0042197 | A1 | | 2/2009 | Hayashizaki et al. | | |
| 2010/0099150 | A1 | | 4/2010 | Fang et al. | | |
| 2011/0250598 | A1 | | 10/2011 | Fischer et al. | | |
| 2015/0159198 | A1 | * | 6/2015 | McGall | ................. | C12Q 1/686 |
| | | | | | | 435/6.11 |
| 2015/0329849 | A1 | * | 11/2015 | Whitney | .................. | C12N 9/96 |
| | | | | | | 435/188 |

FOREIGN PATENT DOCUMENTS

| WO | 99/67371 | 12/1999 | | |
|---|---|---|---|---|
| WO | WO-9967371 A1 | * | 12/1999 | ............... C12N 9/12 |
| WO | 2003/089606 A2 | | 10/2003 | |
| WO | 2008/013885 A2 | | 1/2008 | |
| WO | 2008/152102 A1 | | 12/2008 | |

OTHER PUBLICATIONS

Anarbaev et al., "Klenow fragment and DNA polymerase alpha-primase fromserva calf thymus in water-in-oil nnicroennulsions," Biochimica et Biophysica Acta, vol. 1384, pp. 315-324. (Year: 1998).*

International Search Report and Written Opinion dated Oct. 23, 2015 for International Patent Application No. PCT/US2015/041284, 16 pages.

Ararbaev R O et al., "Klenow fragment and DNA polymerase @a-primase fromserva calf thymus in water-in-oil microemulsions", Biochimica et Biophysica Acta. Protein Structure and Molecular Enzymo, *Elsevier*, Amsterdam; NL, vol. 1384, No. 2, May 19, 1998.

Extended European Search Report from EP Appln. No. 15824160.4, dated Dec. 8, 2017.

* cited by examiner

*Primary Examiner* — Young J Kim

(74) *Attorney, Agent, or Firm* — Kilpatrick Townsend and Stockton LLP

(57) ABSTRACT

Amplification reaction mixtures comprising a cationic surfactant and an anionic surfactant are provided.

18 Claims, 2 Drawing Sheets

Specification includes a Sequence Listing.

BUFFERS FOR USE WITH POLYMERASES

CROSS-REFERENCE TO RELATED PATENT APPLICATIONS

The present patent application claims benefit of priority to U.S. Provisional Patent Application No. 62/027,668, filed on Jul. 22, 2014, which is incorporated by reference.

BACKGROUND OF THE INVENTION

Polymerases are used in a large a number of different molecular reactions, including but not limited to the polymerase chain reaction (PCR).

BRIEF SUMMARY OF THE INVENTION

Provided herein is a solution for storing a polymerase. In some embodiments, the solution comprises a polymerase; an anionic surfactant; and a cationic surfactant. In some embodiments, the concentration of the anionic surfactant and the cationic surfactant is between 0.0001% and 0.1%. In some embodiments, the anionic detergent is sodium dodecyl sulfate (SDS). In some embodiments, the cationic detergent is cetyl trimethylammonium bromide (CTAB). In some embodiments, the anionic detergent is SDS and the cationic detergent is CTAB.

In some embodiments, the solution further comprises a zwitterionic surfactant. In some embodiments, the zwitterionic surfactant is 3-[(3-cholamidopropyl)dimethylammonio]-1-propanesulfonate (CHAPS). In some embodiments, the concentration of the zwitterionic surfactant is 0.01-1.0%.

In some embodiments, wherein the polymerase is thermostable.

Also provided is a reaction mixture comprising a polymerase, an anionic surfactant, and a cationic surfactant. In some embodiments, the reaction mixture further comprises a nucleic acid sample. In some embodiments, the reaction mixture further comprises at least one of nucleotides or oligonucleotide primers, a buffer suitable for polymerase chain reaction (PCR), and magnesium.

In some embodiments, the concentration of the anionic surfactant and the cationic surfactant is between 0.0001% and 0.1%. In some embodiments, the anionic detergent is sodium dodecyl sulfate (SDS). In some embodiments, the cationic detergent is cetyl trimethylammonium bromide (CTAB). In some embodiments, the anionic detergent is SDS and the cationic detergent is CTAB.

In some embodiments, the reaction mixture further comprises a zwitterionic surfactant. In some embodiments, the zwitterionic surfactant is 3-[(3-cholamidopropyl)dimethylammonio]-1-propanesulfonate (CHAPS). In some embodiments, the concentration of the zwitterionic surfactant is 0.01-1.0%.

In some embodiments, the polymerase is thermostable.

Also provided is a method of performing a primer extension reaction. In some embodiments, the method comprises
forming a reaction mixture comprising: a nucleic acid sample that may comprise a target sequence; a primer that anneals to the target sequence; a polymerase; an anionic surfactant; and a cationic surfactant;
annealing the primer to the target sequence, if present; and
extending the primer by at least one nucleotide with the polymerase.

In some embodiments, the extending comprises thermocyclic conditions. In some embodiments, the extending comprises the polymerase chain reaction (PCR).

In some embodiments, the concentration of the anionic surfactant and the cationic surfactant is between 0.0001% and 0.1%. In some embodiments, the anionic detergent is sodium dodecyl sulfate (SDS). In some embodiments, the cationic detergent is cetyl trimethylammonium bromide (CTAB). In some embodiments, the anionic detergent is SDS and the cationic detergent is CTAB.

In some embodiments, the reaction mixture further comprises a zwitterionic surfactant In some embodiments, the zwitterionic surfactant is 3-[(3-cholamidopropyl)dimethylammonio]-1-propanesulfonate (CHAPS). In some embodiments, the concentration of the zwitterionic surfactant is 0.01-1.0%.

In some embodiments, the polymerase is thermostable.

Also provided are kits comprising a polymerase, an anionic surfactant, and a cationic surfactant. In some embodiments, a first container contains the polymerase and a second container comprises the anionic surfactant and the cationic surfactant. In some embodiments, a container comprises polymerase, the anionic surfactant, and the cationic surfactant. In some embodiments, an anionic surfactant, and a cationic surfactant are at a stock solution concentration. In some embodiments, the concentration of the anionic surfactant and the cationic surfactant is between 0.0001% and 0.1%. In some embodiments, the anionic detergent is sodium dodecyl sulfate (SDS). In some embodiments, the cationic detergent is cetyl trimethylammonium bromide (CTAB). In some embodiments, ein the anionic detergent is SDS and the cationic detergent is CTAB. In some embodiments, the kit further comprises a zwitterionic surfactant. In some embodiments, the zwitterionic surfactant is 3-[(3-cholamidopropyl)dimethylammonio]-1-propanesulfonate (CHAPS). In some embodiments, the concentration of the zwitterionic surfactant is 0.01-1.0%. In some embodiments, the polymerase is thermostable.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization described below are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art.

"Surfactants" are compounds that lower the surface tension (or interfacial tension) between two liquids or between a liquid and a solid. Surfactants may act as detergents, wetting agents, emulsifiers, foaming agents, and dispersants. Surfactants are usually organic compounds that are amphiphilic.

The term "Sso7" or "Sso7 DNA binding domain" or "Sso7-like DNA binding domain" or "Sso7 domain" refers to nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, 91%, 92%, 93%, 94%, 95%, 96%, 97%, 98% or 99% or greater amino acid sequence identity to SEQ ID NO:4 or SEQ ID NO:10 of WO2012/177695; or (2) specifically hybridize under stringent hybridization conditions to a Sso7d nucleic acid sequence encoding SEQ ID NO:4 or SEQ ID NO:10 of WO WO2012/177695; and conservatively modified variants thereof. The term includes both full-length Sso7d polypeptides and fragments of the polypeptides that have sequence non-specific double-stranded binding activity. Sso7-like proteins include, but are not limited to, Sso7d, Sac7d and Sac7e. Various Sso7d mutant domains providing increased specificity over wildtype Sso7d are described in, e.g., WO2012/138417 and WO2012/138416.

"Domain" refers to a unit of a protein or protein complex, comprising a polypeptide subsequence, a complete polypeptide sequence, or a plurality of polypeptide sequences where that unit has a defined function. The function is understood to be broadly defined and can be ligand binding, catalytic activity or can have a stabilizing effect on the structure of the protein.

"Heterologous", when used with reference to portions of a protein, indicates that the protein comprises two or more domains that are not found in the same relationship to each other in nature. Such a protein, e.g., a fusion protein, contains two or more domains from unrelated proteins arranged to make a new functional protein.

"Join" refers to any method known in the art for functionally connecting protein domains, including without limitation recombinant fusion with or without intervening domains, intein-mediated fusion, non-covalent association, and covalent bonding, including disulfide bonding; hydrogen bonding; electrostatic bonding; and conformational bonding, e.g., antibody-antigen, and biotin-avidin associations.

"Thermally stable polymerase" or "thermostable polymerase" as used herein refers to any enzyme that catalyzes polynucleotide synthesis by addition of nucleotide units to a nucleotide chain using DNA or RNA as a template and has an optimal activity at a temperature above 45° C.

"*Thermus* polymerase" refers to a family A DNA polymerase isolated from any *Thermus* species, including without limitation *Thermus aquaticus*, *Thermus brockianus*, and *Thermus thermophilus*; any recombinant polymerases deriving from *Thermus* species, and any functional derivatives thereof, whether derived by genetic modification or chemical modification or other methods known in the art.

The term "amplification reaction" refers to any in vitro means for multiplying the copies of a target sequence of nucleic acid. Such methods include but are not limited to polymerase chain reaction (PCR), DNA ligase chain reaction (see U.S. Pat. Nos. 4,683,195 and 4,683,202; PCR Protocols: A Guide to Methods and Applications (Innis et al., eds, 1990)), (LCR), QBeta RNA replicase, and RNA transcription-based (such as TAS and 3SR) amplification reactions as well as others known to those of skill in the art.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing.

The term "amplification reaction mixture" refers to an aqueous solution comprising the various reagents used to amplify a target nucleic acid. These include enzymes, aqueous buffers, salts, amplification primers, target nucleic acid, and nucleoside triphosphates. As discussed further herein, amplification reaction mixtures may also further include stabilizers and other additives to optimize efficiency and specificity. Depending upon the context, the mixture can be either a complete or incomplete (e.g., lacking a nucleic acid template, primers, or both) amplification reaction mixture "Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and serves as a point of initiation of nucleic acid synthesis. Primers can be of a variety of lengths and are often less than 50 nucleotides in length, for example 12-30 nucleotides, in length. The length and sequences of primers for use in PCR can be designed based on principles known to those of skill in the art, see, e.g., Innis et al., supra.

A "template" refers to a polynucleotide sequence that comprises the polynucleotide to be amplified, flanked by primer hybridization sites. Thus, a "target template" comprises the target polynucleotide sequence flanked by hybridization sites for a 5' primer and a 3' primer.

As used herein, "nucleic acid" means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore (e.g., quantum dot) or another moiety.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., a carbon atom that is bound to a hydrogen atom, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The term "encoding" refers to a polynucleotide sequence encoding one or more amino acids. The term does not require a start or stop codon. An amino acid sequence can be encoded in any one of six different reading frames provided by a polynucleotide sequence.

The term "promoter" refers to regions or sequence located upstream and/or downstream from the start of transcription and which are involved in recognition and binding of RNA polymerase and other proteins to initiate transcription.

A "polymerase" refers to an enzyme that performs template-directed synthesis of polynucleotides, e.g., DNA and/or RNA. The term encompasses both the full length polypeptide and a domain that has polymerase activity. DNA polymerases are well-known to those skilled in the art, including but not limited to DNA polymerases isolated or derived from *Pyrococcus furiosus, Thermococcus litoralis*, and *Thermotoga maritime*, or modified versions there of. They include both DNA-dependent polymerases and RNA-dependent polymerases such as reverse transcriptase. At least five families of DNA-dependent DNA polymerases are known, although most fall into families A, B and C. There is little or no sequence similarity among the various families. Most family A polymerases are single chain proteins that can contain multiple enzymatic functions including polymerase, 3' to 5' exonuclease activity and 5' to 3' exonuclease activity. Wildtype Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε, are implicated in nuclear replication, and a family A polymerase, polymerase γ, is used for mitochondrial DNA replication. Other types of DNA polymerases include phage polymerases or fusions between two or more polymerases. Similarly, RNA polymerases typically include eukaryotic RNA polymerases I, II, and III, and bacterial RNA polymerases as well as phage and viral polymerases. RNA polymerases can be DNA-dependent and RNA-dependent.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers &

Miller, Computer Applic. Biol. Sci. 4:11-17 (1988) e.g., as implemented in the program PC/GENE (Intelligenetics, Mountain View, Calif., USA).

Sequences are "substantially identical" to each other if they have a specified percentage of nucleotides or amino acid residues that are the same (e.g., at least 60%, 65%, 70%, 75%, 80%, 85%, 90%, 91%, 92%, 93%, 94%, 95%, 96%, 97%, 98%, or 99% identity over a specified region), when compared and aligned for maximum correspondence over a comparison window, or designated region as measured using one of the following sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Accelrys), or by manual alignment and visual inspection.

Algorithms suitable for determining percent sequence identity and sequence similarity are the BLAST and BLAST 2.0 algorithms, which are described in Altschul et al. (*Nuc. Acids Res.* 25:3389-402, 1977), and Altschul et al. (*J. Mol. Biol.* 215:403-10, 1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=-4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, highly stringent conditions are selected to be about 5-10° C. lower than the thermal melting point ($T_m$) for the specific sequence at a defined ionic strength pH. Low stringency conditions are generally selected to be about 15-30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Hybridization conditions are typically those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Exemplary "stringent hybridization conditions" include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

DETAILED DESCRIPTION OF THE INVENTION

Figure 1:
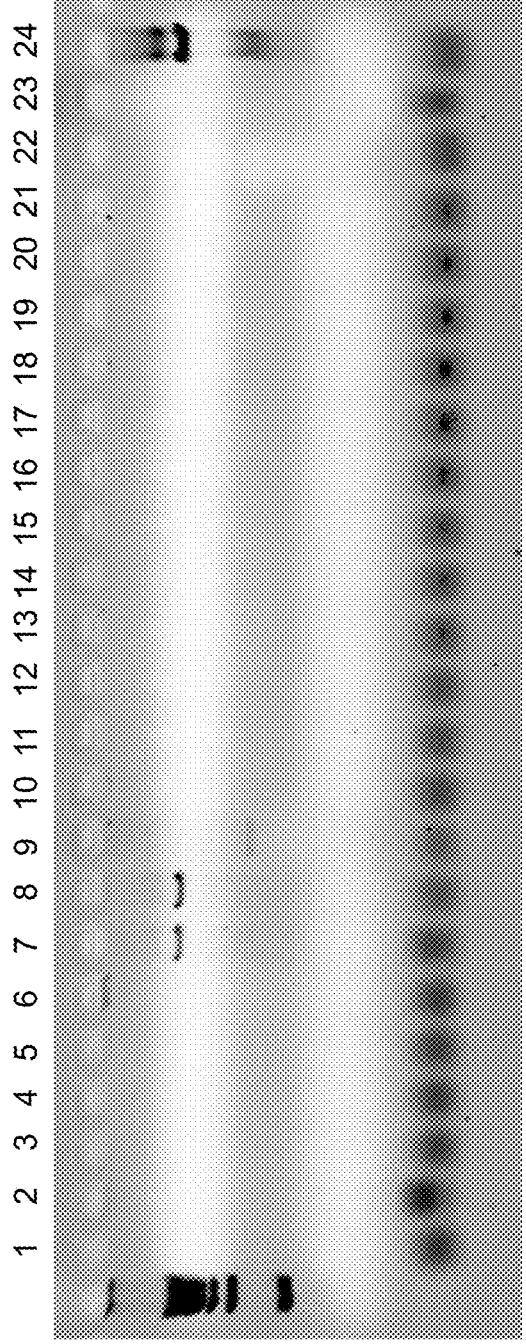
FIG. 1 shows the results of amplification reactions submitted to electrophoresis in an agarose gel. The identity of each reaction is provided in Table 1 in the Examples.

The inventor has surprisingly discovered that inclusion of an anionic surfactant and a cationic surfactant in an amplification reaction results in improved amplification yield compared the absence of only one of the two surfactants or the absence of both. Indeed, as shown in FIG. 1, inclusion of only an anionic surfactant (e.g., SDS) or only a cationic surfactant (e.g., CTAB) does not provide any apparent benefit in an amplification reaction. In contrast, inclusion of both an anionic and cationic surfactant resulted in high amplification yields. Further, it has been discovered that the anionic and cationic surfactant can be stored at high concentration together in the presence of a zwitterionic surfactant (e.g., CHAPs) to maintain solubility of the anionic and cationic surfactants while allowing for their use in amplification reactions from a higher concentration stock solution. Accordingly, in some embodiments, reaction mixtures and amplification reaction stock solutions comprising an anionic and cationic surfactant, and optionally also a zwitterionic surfactant, as well as methods for their use are provided.

Anionic surfactants are surfactants that carry a net negative charge, e.g., a pH 7. Exemplary anionic surfactants include, but are not limited to, sodium dodecyl sulfate (SDS), sodium lauryl sulfate, sodium dodecylbenzenesulfonate, perfluorooctanoic acid, potassium lauryl sulfate, lithium lauryl sulfate, perfluorobutanesulfonic acid, perfluorononanoic acid, perfluorooctanesulfonic acid, dioctyl sodium sulfosuccinate, ammonium lauryl sulfate, sodium lauroyl sarcosinate, sodium myreth sulfate, sodium pareth sulfate, sodium stearate.

Cationic surfactants are surfactants that carry a positive negative charge, e.g., at pH 7. Exemplary cationic surfactants include, but are not limited to, cetyl trimethylammonium bromide (CTAB), surfactants having pH-dependent primary, secondary or tertiary amines, such as octenidine dihydrochloride, or alkyltrimethylammonium salts (e.g., CTAB or cetyl trimethylammonium chloride (CTAC)), or cetylpyridinium chloride (CPC), trimethyl(tetradecyl) ammonium bromide (TTAB), benzalkonium chloride (BAC), benzethonium chloride (BZT), 5-Bromo-5-nitro-1, 3-dioxane, dimethyldioctadecylammonium chloride, cetrimonium bromide, or dioctadecyldimethylammonium bromide (DODAB).

The anionic surfactant concentration in a reaction mixture can be adjusted as needed to optimize amplification yield. In some embodiments, the anionic and cationic surfactant are provided in a reaction mixture at the same concentration, or wherein the concentration of one of the surfactants is no more than 5%, 10%, or 20% different from the other surfactant. For example, one or both of the anionic and cationic surfactant can be at a concentration of 0.0001%-0.1%, e.g., 0.001-0.1%, e.g., 0.01%, 0.02%, 0.03%, 0.04%, 0.05%, 0.06%, 0.07%, 0.08%, or 0.09% or as described elsewhere herein.

In some embodiments, the reaction mixtures or stock solutions further comprise a zwitterionic surfactant. Exemplary zwitterionic surfactants include, but are not limited to, 3-[(3-cholamidopropyl)dimethylammonio]-1-propanesulfonate (CHAPS), 3-([3-Cholamidopropyl]dimethylammonio)-2-hydroxy-1-propanesulfonate (CHAPSO). In some embodiments, the zwitterionic surfactant is at a concentration of between 0.001-1%, e.g., 0.001-0.01% or 0.01-0.1%.

In general it is believed that essentially any polymerase can be included in a reaction mixture comprising the anionic and cationic surfactant to improve amplification yield. In one exemplary embodiment, the polymerase comprises a polymerase domain derived from two parental polymerases, Pfu and DeepVent. Such polymerases are described for example in U.S. Application Publication Nos. 20040219558; 20040214194; 20040191825; 20030162173, each of which is hereby incorporated by reference.

A variety of polymerases can be used in the reaction mixture, or alternatively as at least a portion of a polymerase domain of a hybrid polymerase in the reaction mixture. At least five families of DNA-dependent DNA polymerases are known, although most fall into families A, B and C. There is little or no structural or sequence similarity among the various families. Most family A polymerases are single chain proteins that can contain multiple enzymatic functions including polymerase, 3' to 5' exonuclease activity and 5' to 3' exonuclease activity. Wildtype Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I (family A), II (family B), and III (family C). In eukaryotic cells, three different family B polymerases, DNA polymerases α, δ, and ε are implicated in nuclear replication, and a family A polymerase, polymerase γ, is used for mitochondrial DNA replication. Other types of DNA polymerases include phage polymerases. Any of these polymerases, combinations of all or portions of these polymerases, as well as chimeras or hybrids between two or more of such polymerases or their equivalents can be used to form a portion or all of a polymerase domain for use in the mixtures described herein.

In some embodiments, polymerases comprise one or more mutations that render the polymerase exonuclease deficient. "Exonuclease deficient" as used herein means that the polymerase has a substantially reduced (i.e., less than 10%, 5% or 1% of the 3'-5' exonuclease activity of Pfu DNA polymerase from *Pyrococcus furiosus*) or no exonuclease activity. For example, a double point mutation in the polymerase domain substituting an alanine at positions D141 and E143 can remove or eliminate 3'-5' exonuclease activity. See, e.g., Derbyshire et al., *Methods in Enzymology*, Vol 262 (1995), pages 363-385. Hybrid (e.g., fused to a sequence non-specific double-stranded DNA binding domain) polymerases comprising such double point mutations will generally show an increased specificity in nucleic acid amplification reactions, resulting in fewer amplification byproducts (such as amplification of primer-dimers) and increased efficiency in amplification of the desired target nucleic acids.

In some embodiments, the polymerases are fused to a DNA binding domain. Such fusions are sometimes referred to herein as "hybrid polymerases." A DNA binding domain is a protein, or a defined region of a protein, that binds to nucleic acid in a sequence-independent matter, e.g., binding does not exhibit a gross preference for a particular sequence. DNA binding domains may bind single or double stranded nucleic acids.

The DNA binding proteins of use in the invention are generally thermostable. Examples of such proteins include, but are not limited to, the Archaeal small basic DNA binding proteins Sso7d and Sso7d-like proteins (see, e.g., Choli et al., *Biochimica et Biophysica Acta* 950:193-203, 1988; Baumann et al., *Structural Biol.* 1:808-819, 1994; and Gao et al, *Nature Struc. Biol.* 5:782-786, 1998), Archaeal HMf-like proteins (see, e.g., Starich et al., *J. Molec. Biol.* 255:187-203, 1996; Sandman et al., *Gene* 150:207-208, 1994), and PCNA homologs (see, e.g., Cann et al., *J. Bacteriology* 181:6591-6599, 1999; Shamoo and Steitz, *Cell:* 99, 155-166, 1999; De Felice et al., *J. Mol. Biol.* 291, 47-57, 1999; and Zhang et al., *Biochemistry* 34:10703-10712, 1995).

The HMf-like proteins are archaeal histones that share homology both in amino acid sequences and in structure with eukaryotic H4 histones, which are thought to interact directly with DNA. The HMf family of proteins form stable dimers in solution, and several HMf homologs have been identified from thermostable species (e.g., *Methanothermus fervidus* and *Pyrococcus* strain GB-3a). The HMf family of proteins, once joined to DNA polymerase or any DNA modifying enzyme with a low intrinsic processivity, can enhance the ability of the enzyme to slide along the DNA substrate and thus increase its processivity. For example, the dimeric HMf-like protein can be covalently linked to the N terminus of Taq DNA polymerase, e.g., via chemical modification, and thus improve the processivity of the polymerase.

Certain helix-hairpin-helix motifs have been shown to bind DNA nonspecifically and enhance the processivity of a DNA polymerase to which it is fused (Pavlov et al., *Proc Natl Acad Sci USA* 99:13510-5, 2002).

Sso7d and Sso7d-like proteins, Sac7d and Sac7d-like proteins, e.g., Sac7a, Sac7b, Sac7d, and Sac7e are small (about 7,000 kd MW), basic chromosomal proteins from the hyperthermophilic archaebacteria *Sulfolobus solfataricus* and *S. acidocaldarius*, respectively. These proteins are lysine-rich and have high thermal, acid and chemical stability. They bind DNA in a sequence-independent manner and when bound, increase the $T_m$ of DNA by up to 40° C. under some conditions (McAfee, *Biochemistry* 34:10063-10077, 1995; Gao et al., *Nat. Struct. Biol.* 5(9):782-786, 1998). These proteins and their homologs are typically believed to be involved in stabilizing genomic DNA at elevated temperatures. Suitable Sso7d-like DNA binding domains for use in the invention can be modified based on their sequence homology to Sso7d. Typically, DNA binding domains that are identical to or substantially identical to a known DNA binding protein over a comparison window of about 25 amino acids, optionally about 50-100 amino acids, or the length of the entire protein, can be used in the invention. The sequence can be compared and aligned for maximum correspondence over a comparison window, or designated region as measured using one of the described comparison algorithms or by manual alignment and visual inspection. In some embodiments, the DNA binding domain comprises SEQ ID NO:4 or SEQ ID NO:10 of WO2012/177695 or a substantially (e.g., at least 60%, 70%, 80%, 90%, or 95%) identical sequence thereof. A variety of mutations in the Sso7 binding domain have been described in, e.g., US Patent Application Nos. 2005/0048530 and 2007/0141591.

Additional DNA binding domains suitable for use can be identified by homology with known DNA binding proteins and/or by antibody crossreactivity, or may be found by means of a biochemical assay. DNA binding domains may be synthesized or isolated using the techniques described herein and known in the art.

Sequence non-specific doubled-stranded nucleic acid binding domains for use in the invention can also be identified by cross-reactivity using antibodies, including but not limited to polyclonal antibodies, that bind to known nucleic acid binding domains. Polyclonal antibodies are generated using methods well known to those of ordinary skill in the art (see, e.g., Coligan, Current Protocols in Immunology (1991); Harlow & Lane, Antibodies, A Laboratory Manual (1988)). Those proteins that are immunologically cross-reactive binding proteins can then be detected by a variety of assay methods. For descriptions of various formats and conditions that can be used, see, e.g., Methods in Cell Biology: Antibodies in Cell Biology, volume 37 (Asai, ed. 1993), Coligan, supra, and Harlow & Lane, supra.

Specificity for binding to double-stranded nucleic acids can be tested using a variety of assays known to those of ordinary skill in the art. These include such assays as filter binding assays or gel-shift assays. For example, in a filter-binding assay the polypeptide to be assessed for binding activity to double-stranded DNA is pre-mixed with radiolabeled DNA, either double-stranded or single-stranded, in the appropriate buffer. The mixture is filtered through a membrane (e.g., nitrocellulose) which retains the protein and the protein-DNA complex. The amount of DNA that is retained on the filter is indicative of the quantity that bound to the protein. Binding can be quantified by a competition analysis in which binding of labeled DNA is competed by the addition of increasing amounts of unlabelled DNA. A polypeptide that binds double-stranded DNA at a 10-fold or greater affinity than single-stranded DNA is defined herein as a double-stranded DNA binding protein. Alternatively, binding activity can be assessed by a gel shift assay in which radiolabeled DNA is incubated with the test polypeptide. The protein-DNA complex will migrate slower through the gel than unbound DNA, resulting in a shifted band. The amount of binding is assessed by incubating samples with increasing amounts of double-stranded or single-stranded unlabeled DNA, and quantifying the amount of radioactivity in the shifted band.

A binding domain suitable for use in the invention binds to double-stranded nucleic acids in a sequence-independent fashion, i.e., a binding domain of the invention binds double-stranded nucleic acids with a significant affinity, but, there is no known nucleic acid that binds to the domain with more than 100-fold more affinity than another nucleic acid with the same nucleotide composition, but a different nucleic acid sequence. Non-specific binding can be assayed using methodology similar to that described for determining double-stranded vs. single-stranded nucleic acid binding. Filter binding assays or gel mobility shift assays can be performed as above using competitor DNAs of the same nucleotide composition, but different nucleic acid sequences to determine specificity of binding.

Sequence non-specific double-stranded nucleic acid binding domains for use in the invention can also be assessed, for example, by assaying the ability of the double-stranded binding domain to increase processivity or efficiency of a modifying enzyme or to increase the stability of a nucleic acid duplex by at least 1° C. can be determined.

A binding domain of the invention can also be identified by direct assessment of the ability of such a domain to stabilize a double-stranded nucleic acid conformation. For example, a melting curve of a primer-template construct can be obtained in the presence or absence of protein by monitoring the UV absorbance of the DNA at 260 nm. The $T_m$ of the double-stranded substrate can be determined from the midpoint of the melting curve. The effect of the sequence-non-specific double-stranded nucleic-acid-binding protein on the $T_m$ can then be determined by comparing the $T_m$ obtained in the presence of the modified enzyme with that in the presence of the unmodified enzyme. (The protein does not significantly contribute to the UV absorbance because it has a much lower extinction coefficient at 260 nm than DNA). A domain that increases the $T_m$ by 1° C., often by 5° C., 10° C. or more, can then be selected for use in the invention.

Novel sequence non-specific double-stranded nucleic acid binding proteins can also be isolated by taking advantage of their DNA binding activity, for instance by purification on DNA-cellulose columns. The isolated proteins can then be further purified by conventional means, sequenced, and the genes cloned by conventional means via PCR. Proteins overexpressed from these clones can then be tested by any of the means described above.

A DNA polymerase can be joined to a sequence non-specific DNA binding domain by methods well known to those of skill in the art. These methods include both chemical and recombinant means.

Chemical linking of the DNA polymerase to the non-specific DNA binding domain can be performed, for example, as described in Bioconjugate Techniques, Hermanson, Ed., Academic Press (1996). Joining can include, for example, derivitization for the purpose of linking the two proteins to each other, either directly or through a linking compound, by methods that are well known in the art of protein chemistry. For example, in one chemical conjugation embodiment, the means of linking the catalytic domain and the nucleic acid binding domain comprises a heterobifunctional-coupling reagent which ultimately contributes to formation of an intermolecular disulfide bond between the two moieties. Other types of coupling reagents that are useful in this capacity for the present invention are described, for example, in U.S. Pat. No. 4,545,985. Alternatively, an intermolecular disulfide may conveniently be formed between cysteines in each moiety, which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages.

Linking the DNA polymerase to the non-specific DNA binding domain may also comprise a peptidyl bond formed between moieties that are separately synthesized by standard peptide synthesis chemistry or recombinant means. The conjugate protein itself can also be produced using chemical methods to synthesize an amino acid sequence in whole or in part. For example, peptides can be synthesized by solid phase techniques, such as, e.g., the Merrifield solid phase synthesis method, in which amino acids are sequentially added to a growing chain of amino acids (see, Merrifield (1963) *J. Am. Chem. Soc.*, 85:2149-2146). Equipment for automated synthesis of polypeptides is commercially available from suppliers such as PE Corp. (Foster City, Calif.), and may generally be operated according to the manufacturer's instructions. The synthesized peptides can then be cleaved from the resin, and purified, e.g., by preparative high performance liquid chromatography (see Creighton, Proteins Structures and Molecular Principles, 50-60 (1983)). The composition of the synthetic polypeptides or of sub-fragments of the polypeptide, may be confirmed by amino acid analysis or sequencing (e.g., the Edman degradation procedure; see Creighton, Proteins, Structures and Molecular Principles, pp. 34-49 (1983)).

In addition, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxy-proline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, N-methyl amino acids, and amino acid analogs in general. Furthermore, the amino acid can be D (dextrorotary) or L (levorotary).

In another embodiment, the DNA polymerase and the non-specific DNA binding domain are joined via a linking group. The linking group can be a chemical crosslinking agent, including, for example, succinimidyl-(N-maleimidomethyl)-cyclohexane-1-carboxylate (SMCC). The linking group can also be an additional amino acid sequence(s), including, for example, a polyalanine, polyglycine or similarly, linking group.

Alternatively, in some embodiments, the coding sequences of each polypeptide in the hybrid polymerase are directly joined at their amino- or carboxy-terminus via a peptide bond in any order. Alternatively, an amino acid linker sequence may be employed to separate the first and second polypeptide components by a distance sufficient to ensure that each polypeptide folds into its secondary and tertiary structures. Such an amino acid linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Typical peptide linker sequences contain Gly, Ser, Val and Thr residues. Other near neutral amino acids, such as Ala can also be used in the linker sequence. Amino acid sequences which may be usefully employed as linkers include those disclosed in Maratea et al. (1985) Gene 40:39-46; Murphy et al. (1986) Proc. Natl. Acad. Sci. USA 83:8258-8262; U.S. Pat. Nos. 4,935,233 and 4,751,180. The linker sequence may generally be from 1 to about 50 amino acids in length, e.g., 3, 4, 6, or 10 amino acids in length, but can be 100 or 200 amino acids in length. Linker sequences may not be required when the first and second polypeptides have non-essential N-terminal amino acid regions that can be used to separate the functional domains and prevent steric interference.

Other chemical linkers include carbohydrate linkers, lipid linkers, fatty acid linkers, polyether linkers, e.g., PEG, etc. For example, poly(ethylene glycol) linkers are available from Shearwater Polymers, Inc. Huntsville, Ala. These linkers optionally have amide linkages, sulfhydryl linkages, or heterobifunctional linkages.

Other methods of linking the DNA polymerase and the non-specific DNA binding domain include ionic binding by expressing negative and positive tails and indirect binding through antibodies and streptavidin-biotin interactions. (See, e.g., Bioconjugate Techniques, supra). The domains may also be joined together through an intermediate interacting sequence. For example, an Sso7d-interacting sequence, i.e., a sequence that binds to Sso7d, can be joined to a polymerase. The resulting fusion protein can then be allowed to associate non-covalently with the Sso7d to generate an Sso7d-polymerase conjugate.

In some embodiments, a hybrid polymerase of the invention is produced by recombinant expression of a nucleic acid encoding the protein. Such a hybrid polymerase can be made by ligating the appropriate nucleic acid sequences encoding the desired amino acid sequences to each other by methods known in the art, in the proper coding frame, and expressing the product by methods known in the art.

Nucleic acids encoding the domains to be incorporated into the hybrid polymerases of the invention can be obtained using routine techniques in the field of recombinant genetics. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999).

Nucleic acid sequences that encode the DNA polymerase and the non-specific DNA binding domain polypeptides can be obtained using any of a variety of methods. In some embodiments, the nucleic acid sequences encoding the polypeptides are cloned from cDNA and genomic DNA libraries by hybridization with probes, or isolated using amplification techniques with oligonucleotide primers. More commonly, amplification techniques are used to amplify and isolate the Sso7 and polymerase sequences using a DNA or RNA template (see, e.g., Dieffenfach & Dveksler, PCR Primers: A Laboratory Manual (1995)). Alternatively, overlapping oligonucleotides can be produced synthetically and joined to produce one or more of the domains. Nucleic acids encoding catalytic or double-stranded nucleic acid binding domains can also be isolated from expression libraries using antibodies as probes.

In an example of obtaining a nucleic acid encoding a DNA polymerase or non-specific DNA binding domain using PCR, the nucleic acid sequence or subsequence is PCR amplified, using a sense primer containing one restriction site and an antisense primer containing another restriction site. This will produce a nucleic acid encoding the desired domain sequence or subsequence and having terminal restriction sites. This nucleic acid can then be ligated into a vector containing a nucleic acid encoding the second domain and having the appropriate corresponding restriction sites. The domains can be directly joined or may be separated by a linker, or other, protein sequence. Suitable PCR primers can be determined by one of skill in the art using the sequence information provided in GenBank or other sources. Appropriate restriction sites can also be added to the nucleic acid encoding the protein or protein subsequence by site-directed mutagenesis. The plasmid containing the domain-encoding nucleotide sequence or subsequence is cleaved with the appropriate restriction endonuclease and then ligated into an appropriate vector for amplification and/or expression according to standard methods.

Polymerases can be produced using techniques known in the art. Nucleic acids encoding the polymerase, and optionally linked to a DNA binding domain can be obtained using routine techniques in the field of recombinant genetics. Depending on the host cell in which the polymerase is to be expressed, codon optimization can be employed to optimize expression of the polymerase in a particular host cell. Basic texts disclosing the general methods of use in this invention include Sambrook and Russell, Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-1999). Such nucleic acids may also be obtained through in vitro amplification methods such as those described herein and in Berger, Sambrook, and Ausubel, as well as Mullis et al., (1987) U.S. Pat. No. 4,683,202; PCR Protocols A Guide to Methods and Applications (Innis et al., eds) Academic Press Inc. San Diego, Calif. (1990) (Innis); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Natl. Acad. Sci. USA 87, 1874; Lomeli et al. (1989) J. Clin. Chem., 35: 1826; Landegren et al., (1988) Science 241: 1077-1080; Van Brunt (1990) Biotechnology 8: 291-294; Wu and Wallace (1989) Gene 4: 560; and Barringer et al. (1990) Gene 89: 117, each of which is incorporated by reference in its entirety for all purposes and in particular for all teachings related to amplification methods.

Modifications can additionally be made to polymerases without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

In another aspect, the present invention provides for methods of amplifying a target nucleic acid using a polymerase in a reaction buffer comprising a cationic surfactant and an anionic surfactant, an optionally a zwitterionic surfactant. Such amplification reactions include without limitation the polymerase chain reaction (PCR). Polymerase chain reactions that can be conducted using the compositions described herein include, without limitation, reverse-transcription PCR (rt-PCR) and quantitative PCR (qPCR).

In some embodiments, the methods of the present invention are useful for amplifying an amplicon of 0.1-2 kb, 1-5 kb, at least 5 kb, at least 7 kb, at least 10 kb, at least 12 kb, or more.

The amplification methods can be carried out using reaction mixtures that are sufficient for amplifying a nucleic acid molecule (comprising a polymerase) as well as a cationic surfactant and an anionic surfactant. In addition, in some embodiments, an amplification reaction mixture comprises at least one or more of the following components: nucleotide triphosphates, one or more oligonucleotide primers, salt, buffer, water, stabilizer, and DNA-binding dye.

In some embodiments, the amplification methods of the present invention comprise using polymerases with an agent that improves amplification specificity, for example an agent selected from arginine, spermidine, and spermine. In some embodiments, an amplification reaction mixture comprises, in addition to the DNA polymerase or hybrid polymerase, one or more of the following components: nucleotide triphosphates, one or more oligonucleotide primers, salt, buffer, water, stabilizer, and DNA-binding dye; and an agent selected from arginine, spermidine, or spermine.

In some embodiments, an amplification reaction mixture of the present invention comprises: an anionic surfactant and cationic surfactant, e.g., at a concentration as described herein, optionally a zwitterionic surfactant, e.g., at a concentration as described herein, a polymerase at a concentration of about 1 U/ml to about 75 U/ml (e.g., about 1 U/ml, 5 U/ml, 10 U/ml, 15 U/ml, 20 U/ml, 25 U/ml, 30 U/ml, 35 U/ml, 40 U/ml, 45 U/ml, 50 U/ml, 55 U/ml, 60 U/ml, 65 U/ml, 70 U/ml, or 75 U/ml); dNTPs at a concentration of about 0.1 mM to about 10 mM (e.g., about 0.1 mM, 0.2 mM, 0.3 mM, 0.4 mM, 0.5 mM, 0.6 mM, 0.7 mM, 0.8 mM, 0.9 mM, 1 mM, 2 mM, 3 mM, 4 mM, 5 mM, 6 mM, 7 mM, 8 mM, 9 mM, or 10 mM); magnesium, e.g., $MgCl_2$, at a concentration of about 1 mM to about 20 mM (e.g., about 1 mM, 1.5 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, or 20 mM); $(NH_4)_2SO_4$ at a concentration of about 10 mM to about 100 mM (e.g., about 10 mM, 15 mM, 20 mM, 30 mM, 40 mM, 50 mM, 60 mM, 70 mM, 80 mM, 90 mM, or 100 mM); potassium, e.g, KCl, at a concentration of about 50 mM to about 200 mM (e.g., about 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM); a buffer, e.g., Tris pH 8.5-9.5 at a concentration of about 20 mM to about 200 mM (e.g., about 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM). Optionally the reaction mixture can further comprise one or more of the following: a disaccharide, e.g., trehalose, at a concentration of about 100 mM to about 500 mM (e.g., about 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, or 500 mM); one or more osmolytes, e.g, sarcosine, trimethylamine N-oxide (TMAO), dimethylsulfoniopropionate, and trimethylglycine, at a concentration of about 50 mM to about 200 mM (e.g., about 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, or 200 mM); DMSO at a concentration of about 1% to about 10% (e.g., about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%); fluorescein at a concentration of about 0.001% to about 0.01% (e.g., about 0.001%, 0.002%, 0.003%, 0.004%, 0.005%, 0.006%, 0.007%, 0.008%, 0.009%, or 0.01%); DNA binding dye (e.g., cyanine dye) at a concentration of about 0.5× to about 5× (e.g., about 0.5×, 0.6×, 0.7×, 0.8×, 0.9×, 1×, 1.5×, 2×, 2.5×, 3×, 3.5×, 4×, 4.5×, or 5×); and optionally arginine, spermidine, or spermine or a salt thereof at a concentration of about 1 mM to about 100 mM (e.g., about 1 mM, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM).

In addition to reaction mixtures comprising the concentration of ingredients as described above, also provided are stock solutions comprising all or some of the above ingredients, wherein all of the ingredients in the stock solution are 2×, 3×, 5×, 10×, 20×, 25×, 50×, 100×, or another multiple of the above concentrations such that a small amount of the stock solution can be added as a fraction of the total volume of the final reaction mixture. For instance, in some embodiments, a stock solution of a cationic surfactant, an anionic surfactant, nucleotides (e.g., dNTPs), a buffer, magnesium and potassium source and optionally an ammonium sulfate source and/or zwitterionic surfactant such as those listed above can be included in a stock solution. In some embodiments, the polymerase is also included in a stock solution or alternatively, included in a second container such that the polymerase can be added when the reaction is to be performed.

In some embodiments, an amplification reaction furtehr comprises an additive to improve efficiency. Members of the osmolyte family have been shown to improve the thermal stability of proteins (Santoro, Biochemistry, 1992) as well as decrease DNA double helix stability (Chadalavada, FEBS Letters, 1997). In some embodiments, osmolytes are small molecules or compounds which are produced by living organisms in response to environmental stresses such as extreme temperatures, dehydration, or salinity and which protect their cellular components and help to maintain optimal cytosolic conditions. Osmolytes of use in the present invention may include without limitation sarcosine, trimethylamine N-oxide (TMAO), dimethylsulfoniopropionate, and trimethylglycine. Sarcosine is chemically similar to betaine, a chemical which has been shown to improve conventional PCR (Henke, Nucleic Acids Research, 1997).

In conventional uses of osmolytes, the stabilizing effects of such compounds are generally observed at relatively high concentrations (>1 M). However, in methods of the present invention, millimolar concentrations of osmolytes have been found to be effective for improving the reaction efficiency of amplification reactions such as qPCR. Without being bound by a mechanism of action, it is possible that the improvement in efficiency is the result of improving the accessibility of the DNA polymerase to the targeted region of the DNA template for reactions that contain low concentrations of input DNA sample. In some embodiments, concentrations of about 100 to about 1000 mM of osmolytes are used in methods and kits of the present invention. In still further embodiments, concentrations of about 50 to about 700, about 100 to about 600, about 150 to about 500, about 200 to about 400 mM, and about 300 to about 350 mM osmolytes are used in methods and kits of the invention. In some embodiments, the osmolyte used is.

A wide variety of amplification methods can be performed with the reaction mixtures described herein. Such amplification reaction methods can include without limitation polymerase chain reaction (PCR), DNA ligase chain reaction (LCR), QBeta RNA replicase, and RNA transcription-based (such as TAS and 3SR) amplification reactions as well as others known to those of skill in the art. Polymerase chain reactions that can be conducted using the reaction mixtures described herein include without limitation reverse-transcription PCR (rt-PCR) and quantitative PCR (qPCR).

In some embodiments, the PCR is quantitative PCR in which the accumulation of amplicon is monitored in "real time" (i.e., continuously, e.g., once per cycle—rather than only following the completion of amplification). Quantitative amplification methods (e.g., quantitative PCR or quantitative linear amplification) can involve amplification of an nucleic acid template, directly or indirectly (e.g., determining a Ct value) determining the amount of amplified DNA, and then calculating the amount of initial template based on the number of cycles of the amplification. Amplification of a DNA locus using reactions is well known (see U.S. Pat. Nos. 4,683,195 and 4,683,202; PCR PROTOCOLS: A GUIDE TO METHODS AND APPLICATIONS (Innis et al., eds, 1990)). Typically, PCR is used to amplify DNA templates. However, alternative methods of amplification have been described and can also be employed, as long as the alternative methods amplify intact DNA to a greater extent than the methods amplify cleaved DNA. Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol Biotechnol.* 20(2):163-79 (2002).

In some embodiments, quantitative amplification is based on the monitoring of the signal (e.g., fluorescence of a probe) representing copies of the template in cycles of an amplification (e.g., PCR) reaction. In the initial cycles of the PCR, a very low signal is observed because the quantity of the amplicon formed does not support a measurable signal output from the assay. After the initial cycles, as the amount of formed amplicon increases, the signal intensity increases to a measurable level and reaches a plateau in later cycles when the PCR enters into a non-logarithmic phase. Through a plot of the signal intensity versus the cycle number, the specific cycle at which a measurable signal is obtained from the PCR reaction can be deduced and used to back-calculate the quantity of the target before the start of the PCR. The number of the specific cycles that is determined by this method is typically referred to as the cycle threshold (Ct). Exemplary methods are described in, e.g., Heid et al. *Genome Methods* 6:986-94 (1996) with reference to hydrolysis probes.

One method for detection of amplification products is the 5'-3' exonuclease "hydrolysis" PCR assay (also sometimes referred to as the TaqMan™ assay) (U.S. Pat. Nos. 5,210,015 and 5,487,972; Holland et al., *PNAS USA* 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (e.g., the "TaqMan™ probe) during the amplification reaction. The fluorogenic probe consists of an oligonucleotide labeled with both a fluorescent reporter dye and a quencher dye. During PCR, this probe is cleaved by the 5'-3' exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer, *Nature Biotech.* 14:303-309 (1996), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in the open conformation and fluorescence is detected, while those that remain unhybridized will not fluoresce (Tyagi and Kramer, *Nature Biotechnol.* 14: 303-306 (1996)). As a result, the amount of fluorescence will increase as the amount of PCR product increases, and thus may be used as a measure of the progress of the PCR. Those of skill in the art will recognize that other methods of quantitative amplification are also available.

Various other techniques for performing quantitative amplification of a nucleic acids are also known. For example, some methodologies employ one or more probe oligonucleotides that are structured such that a change in fluorescence is generated when the oligonucleotide(s) is hybridized to a target nucleic acid. For example, one such method involves is a dual fluorophore approach that exploits fluorescence resonance energy transfer (FRET), e.g., Light-Cycler™ hybridization probes, where two oligo probes anneal to the amplicon. The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: Scorpions™ probes (e.g., Whitcombe et al., *Nature Biotechnology* 17:804-807, 1999, and U.S. Pat. No. 6,326,145); Sunrise™ (or Amplifluor™) probes (e.g., Nazarenko et al., *Nuc. Acids Res.* 25:2516-2521, 1997, and U.S. Pat. No. 6,117,635), and probes that form a secondary structure that results in reduced signal without a quencher and that emits increased signal when hybridized to a target (e.g., Lux Probes™)

In some embodiments, the PCR reaction mixture does not include a labeled probe oligonucleotide. For example, the reaction mixture lacks a Taqman or other labeled oligonucleotide probe for monitoring real-time or endpoint accumulation of the amplicon. In some of these embodiments, an intercalating fluorescent dye is included. In some embodiments, the intercalating dye changes signal (increases or decreases) when bound to double stranded nucleic acids compared to single stranded nucleic acids. Exemplary agents include SYBR GREEN™, SYBR GOLD™, and EVAGREEN™. Since these agents are not template-specific, it is assumed that the signal is generated based on template-specific amplification. This can be confirmed by monitoring signal as a function of temperature because melting point of template sequences will generally be much higher than or different from, for example, primer-dimers, non-specifically amplified sequences, etc In another aspect, the present invention provides kits for conducting nucleic acid amplification reactions. The kits include a cationic surfactant and an anionic surfactant, typically in the same solution. The solution can further comprise a buffer (e.g., Tris), magnesium and potassium and nucleotides (dNTPs). The solution can optionally also comprise a zitterionic surfactant as described herein. In some embodiments, the kit further comprises a DNA polymerase as described herein either in the same solution or in a separate solution in a separate container. As described above, in some embodiments, the solution comprising the cationic surfactant and anionic surfactant is a stock solution, and thus ingredient concentrations are a multiple (e.g., 2×, 5C, 10×, etc., of the concentration finally desired for the reaction mixture.

Optionally, the kits comprise a double stranded DNA binding dye. Such kits may also include stabilizers and other additives (e.g., sarcosine) to increase the efficiency of the amplification reactions. Such kits may also include one or more primers as well as instructions for conducting nucleic acid amplification reactions using the components of the kits. Optionally, the kit can further comprise a sufficient amount of an agent to improve the specificity of nucleic acid amplification. For example, in some embodiments, the agent is selected from free arginine (e.g., L-arginine or D-arginine), spermidine, and spermine, or a salt thereof.

EXAMPLES

The following examples are offered to illustrate, but not to limit the claimed invention.

The effect of various surfactants on polymerase activity and yield in a PCR reaction mixture was tested. A polymerase derived from two parental polymerases, Pfu and DeepVent, and fused with an Sso7d, was formulated in a variety of reaction mixtures in an effort to identify reaction components that improve PCR yield.

A reaction mixture comprising polymerase, Tris-HCL pH 9.0, KCl, ammonium sulfate, 20 ng template DNA and target primers was tested with one or more additional components added as follows (results shown in FIG. 1):

TABLE 1

| Sample # | Additive | Final Conc. % |
|---|---|---|
| 1 | | |
| 2 | iPFC11 | 7x |
| 3 | SDS | 0.001 |
| 4 | SDS | 0.01 |
| 5 | CTAB | 0.001 |
| 6 | CTAB | 0.01 |
| 7 | SDS + CTAB | 0.001 + 0.001 |
| 8 | SDS + CTAB | 0.01 + 0.01 |
| 9 | ODG | 5 |
| 10 | ODG | 1 |
| 11 | ODG | 0.1 |
| 12 | ODG | 0.01 |
| 13 | NDSB201 | 1 |
| 14 | NDSB201 | 0.1 |
| 15 | NDSB201 | 0.01 |
| 16 | NDSB256 | 1 |
| 17 | NDSB256 | 0.1 |
| 18 | NDSB256 | 0.01 |
| 19 | PEG | 0.1 |
| 20 | PEG | 1 |
| 21 | PVP | 0.1 |
| 22 | PVP | 1 |
| 23 | Glycerol | 30 |
| 24 | Triton X-100 | 0.1 |

As shown in FIG. 1, while SDS, an anionic surfactant, and CTAB, a cationic surfactant, each alone did not improve PCR yield, a combination of the two surfactants surprisingly resulted in an increase in PCR yield (see lanes 7-8 of FIG. 1).

Figure 2:
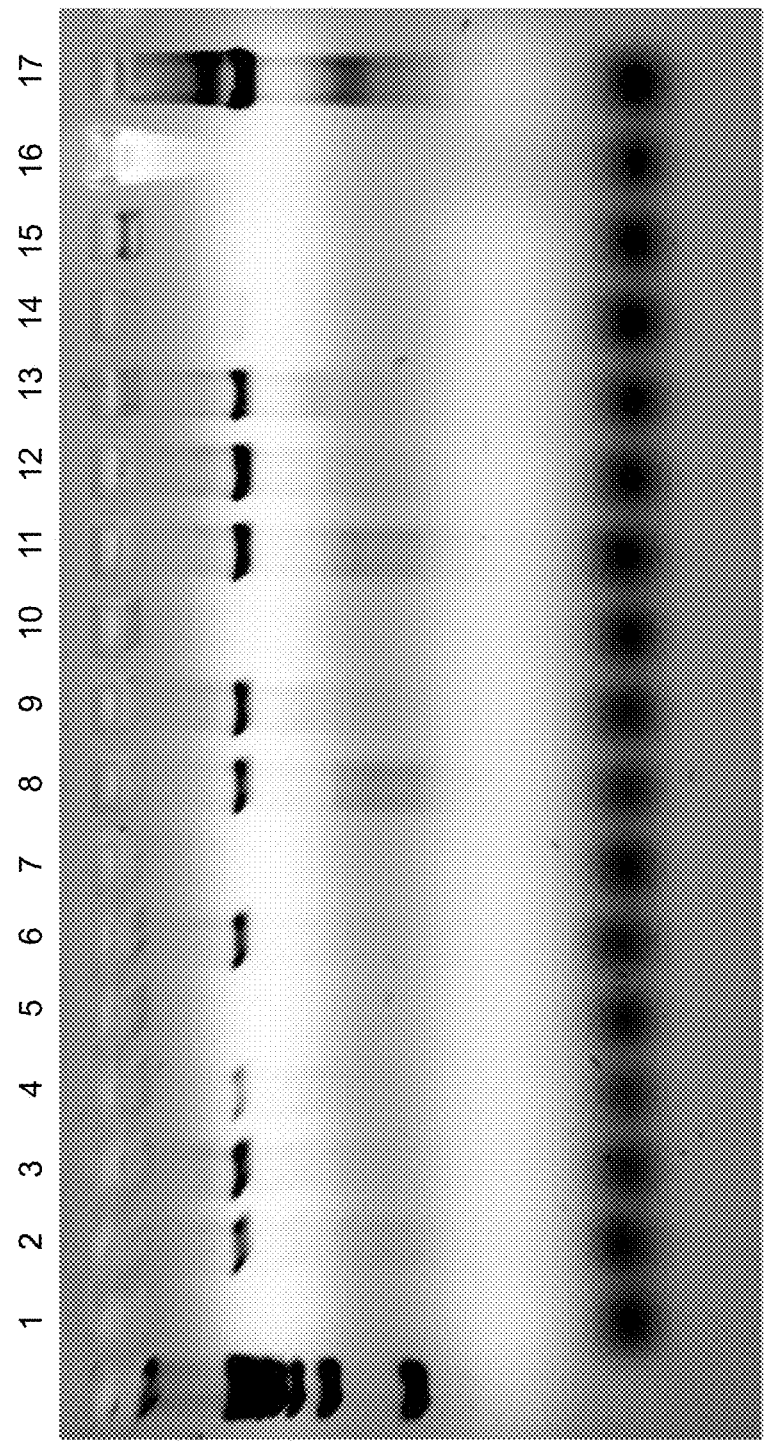
FIG. 2 shows the results of amplification reactions submitted to electrophoresis in an agarose gel. The identity of each reaction is provided in Table 2 in the Examples.

Ranges of concentration of CTAB and SDS were tested and additional components such as octyl b-D-glucopyranoside (OGP) and bovine serum albumin (BSA) were also tested. See, FIG. 2. The lanes of FIG. 2. are described in Table 2 below:

TABLE 2

| Sample # | Additives | Additives1 Final conc | Additives2 Final conc | Additives3 Final conc |
|---|---|---|---|---|
| 1 | Control | | | |
| 2 | SDS + CTAB | 0.001 | 0.001 | |
| 3 | SDS + CTAB | 0.01 | 0.01 | |
| 4 | SDS + CTAB | 0.05 | 0.05 | |
| 5 | SDS + CTAB | 0.1 | 0.1 | |
| 6 | SDS + CTAB | 0.01 | 0.0126 | |
| 7 | SDS + CTAB | 0.02 | 0.0126 | |
| 8 | SDS + CTAB + OGP | 0.001 | 0.001 | 0.001 |
| 9 | SDS + CTAB + OGP | 0.01 | 0.01 | 0.01 |
| 10 | SDS + CTAB + OGP | 0.1 | 0.1 | 0.1 |
| 11 | SDS + CTAB + BSA | 0.001 | 0.001 | 0.1 |
| 12 | SDS + CTAB + BSA | 0.01 | 0.01 | 0.1 |
| 13 | SDS + CTAB + BSA | 0.1 | 0.1 | 0.1 |
| 14 | LS + CTAB | 0.001 | 0.001 | |
| 15 | LS + CTAB | 0.01 | 0.01 | |
| 16 | LS + CTAB | 0.05 | 0.05 | |
| 17 | Triton X-100 | 0.1 | | |

In view of the surprising success of the reaction mixture comprising SDS and CTAB, a 5x stock solution was generated. However, in some cases, a precipitate formed in the stock solution. To address the precipitation, a zwitterionic surfactant, CHAPS, was added to the 5x stock solution and this prevented formation of a precipitate. For example, when the 5x stock solution contained 1% CHAPS, no precipitate was observed in the stock solution. Further, when the 5x stock solution comprising 0.05% SDS and 0.05% CTAB was used in PCR reactions, 2 and 5 kb amplicons were successfully generated, indicating that the presence of CHAPS did not interfere with PCR at this concentration (data not shown).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A solution for storing a polymerase, the solution comprising,
   1-20 mM $Mg^{2+}$;
   a polymerase;
   an anionic surfactant, wherein the concentration of the anionic surfactant is between 0.0001% and 0.1%; and
   a cationic surfactant, wherein the concentration of the cationic surfactant is between 0.0001% and 0.1%.

2. The solution of claim 1, wherein the anionic surfactant is sodium dodecyl sulfate (SDS).

3. The solution of claim 1, wherein the cationic surfactant is cetyl trimethylammonium bromide (CTAB).

4. The solution of claim 1, wherein the anionic surfactant is SDS and the cationic detergent is CTAB.

5. The solution of claim 1, further comprising a zwitterionic surfactant.

6. The solution of claim 5, wherein the zwitterionic surfactant is 3-[(3-cholamidopropyl)dimethylammonio]-1-propanesulfonate (CHAPS).

7. The solution of claim 5, wherein the concentration of the zwitterionic surfactant is 0.01-1.0%.

8. The solution of claim 1, wherein the polymerase is thermostable.

9. A reaction mixture comprising
   1-20 mM $Mg^{2+}$;
   a nucleic acid sample;
   a polymerase;
   an anionic surfactant, wherein the concentration of the anionic surfactant is between 0.0001% and 0.1%; and
   a cationic surfactant, wherein the concentration of the cationic surfactant is between 0.0001% and 0.1%.

10. The reaction mixture of claim 9, further comprising at least one of nucleotides or oligonucleotide primers and a buffer suitable for polymerase chain reaction (PCR).

11. The reaction mixture of claim 9, wherein the anionic surfactant is sodium dodecyl sulfate (SDS).

12. The reaction mixture of claim 9, wherein the cationic surfactant is cetyl trimethylammonium bromide (CTAB).

13. The reaction mixture of claim 9, wherein the anionic surfactant is SDS and the cationic detergent is CTAB.

14. The reaction mixture of claim 9, further comprising a zwitterionic surfactant.

15. The reaction mixture of claim 14, wherein the zwitterionic surfactant is 3-[(3-cholamidopropyl)dimethylammonio]-1-propanesulfonate (CHAPS).

16. A method of performing a primer extension reaction, the method comprising,
    forming a reaction mixture comprising:
    a nucleic acid sample that may comprise a target sequence;
    a primer that anneals to the target sequence; and
    the solution of claim 1;
    annealing the primer to the target sequence, if present; and
    extending the primer by at least one nucleotide with the polymerase.

17. The method of claim 16, wherein the extending comprises thermocyclic conditions.

18. The method of claim 17, wherein the extending comprises the polymerase chain reaction (PCR).

* * * * *

SEQUENCE LISTING

<160> NUMBER OF SEQ ID NOS: 10

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4
<211> LENGTH: 63
<212> TYPE: PRT
<213> ORGANISM: Artificial Sequence
<220> FEATURE:
<223> OTHER INFORMATION: synthetic exemplary non-specific DNA binding
      domain

<400> SEQUENCE: 4

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 64
<212> TYPE: PRT
<213> ORGANISM: Artificial Sequence
<220> FEATURE:
<223> OTHER INFORMATION: synthetic Ss07d/Ssh7A/SsoP2 DNA binding domain

<400> SEQUENCE: 10

Met Ala Thr Val Lys Phe Lys Tyr Lys Gly Glu Glu Lys Glu Val Asp
1               5                   10                  15

Ile Ser Lys Ile Lys Lys Val Trp Arg Val Gly Lys Met Ile Ser Phe
            20                  25                  30

Thr Tyr Asp Glu Gly Gly Gly Lys Thr Gly Arg Gly Ala Val Ser Glu
        35                  40                  45

Lys Asp Ala Pro Lys Glu Leu Leu Gln Met Leu Glu Lys Gln Lys Lys
    50                  55                  60